United States Patent
Yonezawa

(10) Patent No.: US 9,918,624 B2
(45) Date of Patent: Mar. 20, 2018

(54) OPHTHALMIC APPARATUS, PHOTORECEPTOR CELL DETECTION METHOD AND PROGRAM

(71) Applicant: CANON KABUSHIKI KAISHA, Tokyo (JP)

(72) Inventor: Keiko Yonezawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 267 days.

(21) Appl. No.: 14/963,782

(22) Filed: Dec. 9, 2015

(65) Prior Publication Data
US 2016/0174831 A1   Jun. 23, 2016

(30) Foreign Application Priority Data
Dec. 16, 2014   (JP) .................................. 2014-254601

(51) Int. Cl.
  G06K 9/00 (2006.01)
  A61B 3/00 (2006.01)
  A61B 3/14 (2006.01)
  A61B 3/12 (2006.01)
  A61B 3/10 (2006.01)

(52) U.S. Cl.
CPC .......... *A61B 3/0025* (2013.01); *A61B 3/0058* (2013.01); *A61B 3/1025* (2013.01); *A61B 3/12* (2013.01); *A61B 3/14* (2013.01)

(58) Field of Classification Search
None
See application file for complete search history.

(56) References Cited

FOREIGN PATENT DOCUMENTS

JP    2014-121452 A    7/2014

OTHER PUBLICATIONS

K.Y. Li A. Roorda, Automated Identification of Cone Photoreceptors in Adaptive Optics Retinal Images, J. Opt. Soc. Am. A/vol. 24, No. 5/May 2007, pp. 1358-1363.

*Primary Examiner* — Atiba O Fitzpatrick
(74) *Attorney, Agent, or Firm* — Canon U.S.A., Inc. IP Division

(57) ABSTRACT

An ophthalmic apparatus includes an image acquiring unit configured to acquire an eye fundus image of an eye to be examined, a candidate acquiring unit configured to acquire a plurality of candidate points for a photoreceptor cell in the eye fundus image based on brightness values of the eye fundus image, a first acquiring unit configured to acquire a first feature value of a first candidate point included in the plurality of candidate points based on a distance between the first candidate point and a second candidate point included in the plurality of candidate points, and a determining unit configured to determine whether the first candidate point is a point representing the photoreceptor cell or not based on the first feature value.

15 Claims, 10 Drawing Sheets

OPHTHALMIC APPARATUS, PHOTORECEPTOR CELL DETECTION METHOD AND PROGRAM

BACKGROUND

Field

The disclosed art generally relates to an ophthalmic apparatus, a photoreceptor cell detection method and a program.

Description of the Related Art

There has been known an adaptive optics scanning laser ophthalmoscope (hereinafter called an AO-SLO) applying an aberration correction technology to an ophthalmic apparatus. The AO-SLO is an ophthalmoscope applying a telescope technology which acquires a clear image of a star by compensating fluctuations of the atmosphere to the eye and is capable of resolving each one of photoreceptor cells of the retina.

From the clinical value viewpoint, extraction of an effective index for a diagnosis from the image acquired by the AO-SLO may be necessary. There has been a need for a technology for accurately detecting a photoreceptor cell as an effective index from an image. K. Y. Li and A. Roorda, "Automated identification of cone photoreceptors in adaptive optics retinal images," J. Opt. Soc. Am. A 24(5), 1358-1363 (2007) discloses a scheme focusing on a brightness profile of photoreceptor cells, which performs low-pass filtering supporting a frequency corresponding to the cycle of photoreceptor cells on brightness and then detects a maximum value therefrom.

However, because the cited art detects a photoreceptor cell by using the maximum value of brightness of an image, a photoreceptor cell having a low brightness may not be detected. There is also a problem that noise having a high brightness may unintentionally be detected as a photoreceptor cell.

SUMMARY

The present disclosure was made in view of this circumstance and may improve the accuracy of detection of a photoreceptor cell.

Without limiting thereto, the present disclosure may also provide an operational advantage which may be led from configurations according to embodiments of the present invention, which will be described below, and may not be provided by technologies in the past.

An ophthalmic apparatus includes an image acquiring unit configured to acquire an eye fundus image of an eye to be examined, a candidate acquiring unit configured to acquire a plurality of candidate points for a photoreceptor cell in the eye fundus image based on brightness values of the eye fundus image, a first acquiring unit configured to acquire a first feature value of a first candidate point included in the plurality of candidate points based on a distance between the first candidate point and a second candidate point included in the plurality of candidate points, and a determining unit configured to determine whether the first candidate point is a point representing the photoreceptor cell or not based on the first feature value.

Further features of the present disclosure will become apparent from the following description of exemplary embodiments with reference to the attached drawings.

DESCRIPTION OF THE EMBODIMENTS

Image processing devices according to embodiments will be described below with reference to drawings. It should be noted that the configurations according to the embodiments which will be described below are given for illustrative purpose only and that the present invention is not intended to be limited by the following exemplary embodiments.

First Exemplary Embodiment

According to a first exemplary embodiment, an algorithm will be described which selects a detected point in consideration of a positional relationship between candidate points acquired based on brightness values of an AO-SLO image acquired by imaging the retina by using an AO-SLO apparatus to detect a photoreceptor cell (such as a cone) from the image.

First of all, regions having a convex-shaped brightness distribution (i.e. a region having a higher brightness) of the AO-SLO image are detected and are defined as candidate points. Next, feature values corresponding to the size and curvature of each of the candidate points are acquired from pixel information of the neighborhood of the candidate point. Furthermore, a feature value in consideration of the position of each of the candidate points is acquired from the positional relationship between the candidate points. Based on these two types of feature values, a detected point is selected.

Based on both of the local feature value of each of the candidate points and the feature value in consideration of the positional relationship between candidate points, a photoreceptor cell can be detected with high accuracy.

Configuration of Ophthalmic Apparatus

Figure 1:
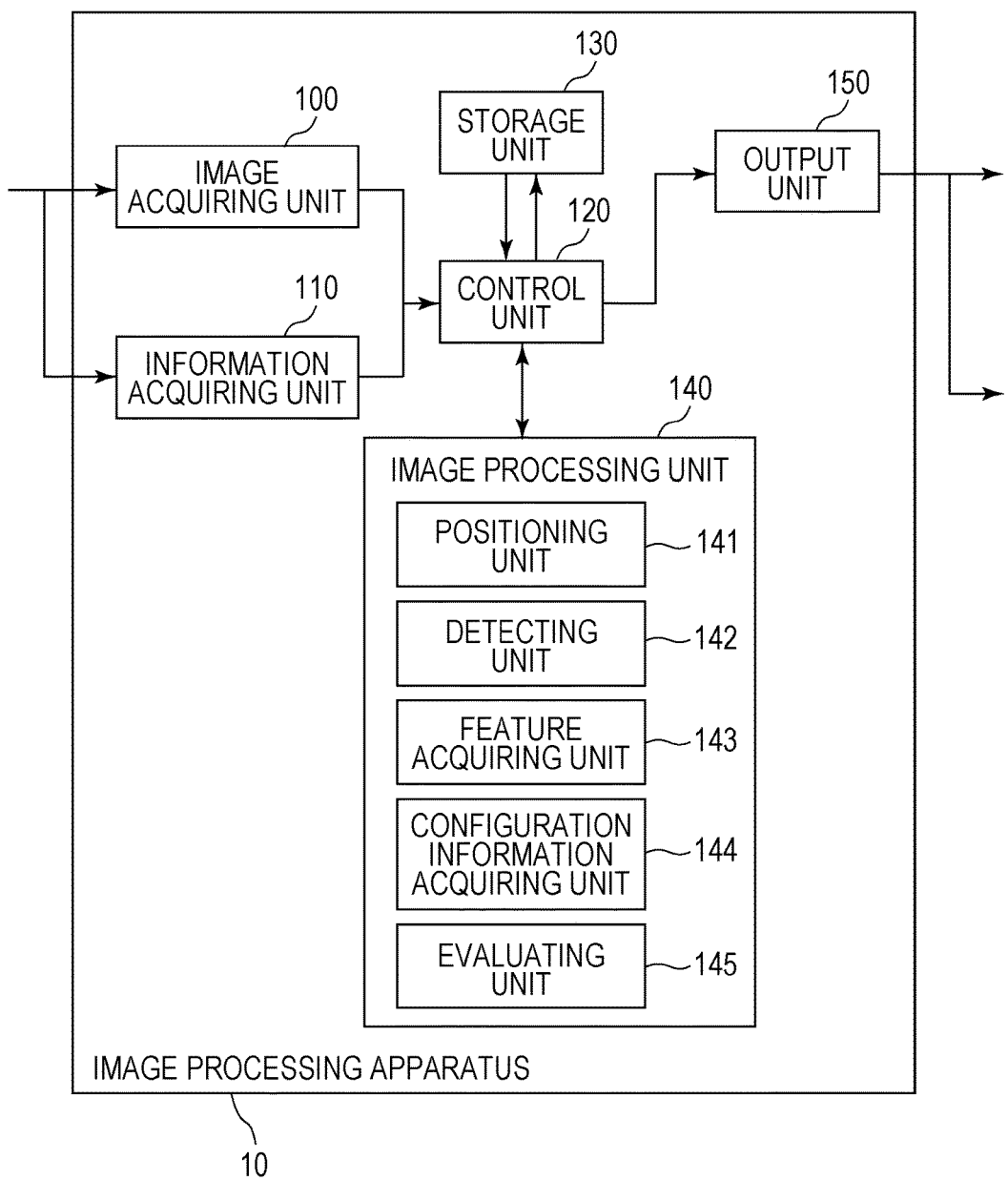
FIG. 1 illustrates an example of a functional configuration of an image processing device according to first exemplary embodiment.

FIG. 1 illustrates a functional configuration of an image processing device 10 according to this exemplary embodiment. The image processing device 10 functions as an image acquiring unit 100, an information acquiring unit 110, a control unit 120, an image processing unit 140, and an output unit 150 illustrated in FIG. 1 through execution of programs stored in a ROM, not illustrated, by a CPU, not illustrated. The image processing unit 140 includes a positioning unit 141, a detecting unit 142, a feature acquiring unit 143, a configuration information acquiring unit 144, and an evaluating unit 145. The positioning unit 141, detecting unit 142, feature acquiring unit 143, configuration information acquiring unit 144, and evaluating unit 145 are also implemented by programs executed by a CPU.

It should be noted that the image processing device 10 may include one or a plurality of CPUs and ROMs. In other words, at least one processing device (CPU) and at least one storage device (such as a ROM) are connected, and when the at least one processing device executes a program stored in the at least one storage device, the image processing device 10 functions as the unit corresponding to the program.

The image acquiring unit 100 acquires a planer image (AO-SLO image) captured by an AO-SLO apparatus, in which an aberration caused by the eyes is corrected. The AO-SLO apparatus generates an AO-SLO image based on return light from the eye fundus of the eye to be examined in which the aberration caused by the eye to be examined has been corrected. In other words, the image acquiring unit 100 corresponds to an example of an image acquiring unit configured to acquire an eye fundus image of an eye to be examined based on return light from the eye to be examined, in which an aberration caused by the eye to be examined is corrected. The AOSLO apparatus may apply the configuration disclosed in Japanese Patent Laid-Open No. 2014-121452, for example, or may apply other configurations.

The image acquiring unit 100 acquires a planer image (Wide Field-SLO image) captured by the AO-SLO apparatus. The planer image has a wider field angle than that of an AO-SLO image. The planer image acquired by the image acquiring unit 100 is stored in the storage unit 130 through the control unit 120.

The information acquiring unit 110 acquires information regarding the eye to be examined and an input from a user.

The control unit 120 stores the planer image acquired by the image acquiring unit 100 and the information regarding the eye to be examined acquired by the information acquiring unit 110 in the storage unit 130.

The storage unit 130 may be an HDD, for example, and is configured to store the planer image acquired by the image acquiring unit 100 and the information regarding the eye to be examined acquired by the information acquiring unit 110. Information regarding a photoreceptor cell acquired by the image processing unit 140 is further stored therein. It should be noted that the storage unit 130 is not limited to the HDD and may be an SSD, for example.

The image processing unit 140 is configured to perform positioning processing for positioning an AO-SLO image with respect to the acquired WF-SLO image. The image processing unit 140 analyzes photoreceptor cells with respect to the AO-SLO image and calculates an index such as the density of photoreceptor cells. The image processing unit 140 includes the positioning unit 141, the detecting unit 142, the feature acquiring unit 143, the configuration information acquiring unit 144, and the evaluating unit 145.

The positioning unit 141 is configured to position an AO-SLO image and a WF-SLO image. More specifically, the AO-SLO image is positioned with reference to the WF-SLO image. The positioning unit 141 after the positioning calculates the distance from the position of the fovea on the WF-SLO image to AO-SLO images positioned with reference to the WF-SLO image. It should be noted that the distance from the fovea to an AO-SLO image may be the distance from the fovea to the center of the AO-SLO image or the distance from the fovea to an edge portion close to (or far from) the fovea of the AO-SLO image.

Because the fovea has a lower brightness than that of the surroundings, the positioning unit 141 is able to detect the fovea based on the brightness of the WF-SLO image, for example. When an AO-SLO image including the fovea is given, the positioning unit 141 may detect the fovea from the AO-SLO image. An operator may designate the fovea with reference to a WF-SLO image or an AO-SLO image.

The detecting unit 142 detects a point where a photoreceptor cell candidate exists (hereinafter, which may be called a candidate point) from an AO-SLO image based on information regarding brightness of the AO-SLO image. In other words, the detecting unit 142 corresponds to an example of a candidate acquiring unit configured to acquire candidate points of a plurality of photoreceptor cells from an eye fundus image based on brightness values of the eye fundus image.

The feature acquiring unit 143 acquires feature values of candidate points detected by the detecting unit 142. Details of how such feature values are acquired will be described below.

The configuration information acquiring unit 144 acquires feature values based on the configuration of the plurality of candidate points detected by the detecting unit 142. For example, the configuration information acquiring unit 144 acquires the distance between two neighboring candidate points of the plurality of candidate points detected by the detecting unit 142. More specifically, the distance between a candidate point neighboring to the candidate point of interest as a feature value of the candidate point of interest. In other words, the configuration information acquiring unit 144 corresponds to an example of a first acquiring unit configured to acquire a first feature value of a first candidate point included in a plurality of candidate points based on a distance between the first candidate point and a second candidate point included in the plurality of candidate points. The second candidate point is a point neighboring to the first candidate point.

Here, the feature value to be acquired by the feature acquiring unit 143 and the feature value calculated by the configuration information acquiring unit 144 are different feature values. For example, while the feature acquiring unit 143 does not acquire a feature value with focus on the position relationship between one candidate point and another candidate point, the configuration information acquiring unit 144 acquires a feature value with focus on the position relationship between one candidate point and another candidate point.

The evaluating unit 145 evaluates whether the candidate point of interest is a point representing a photoreceptor cell or not. More specifically, the evaluating unit 145 evaluates whether the candidate point is a point representing a photoreceptor cell or not based on the feature value acquired by the feature acquiring unit 143 and the feature value acquired by the configuration information acquiring unit 144. In other words, the evaluating unit 145 uses two different feature values to evaluate whether the candidate point of interest is a point representing a photoreceptor cell or not. The evaluating unit 145 corresponds to an example of a determining unit configured to determine whether the first candidate point is a point representing a photoreceptor cell or not based on the first feature value and the second feature value. It should be noted that the evaluating unit 145 may evaluate whether the candidate point is a point representing a photoreceptor cell or not based on the feature value acquired by the configuration information acquiring unit 144 without using the feature value acquired by the feature acquiring unit 143. The evaluating unit 145 corresponds to an example of a determining unit configured to determine whether the first candidate point is a point representing a photoreceptor cell or not based on the first feature value.

The output unit 150 outputs information to a monitor, not illustrated. For example, the output unit 150 causes the monitor to display a point determined as a point representing a photoreceptor cell among the candidate points over the AO-SLO image. In other words, the output unit 150 functions as a display control unit configured to cause a display unit such as a monitor to display information. The output unit 150 corresponds to an example of a display control unit configured to cause a display unit to display a candidate point determined as a point representing a photoreceptor cell by the determining unit and the eye fundus image.

Planer Image

Figure 3:
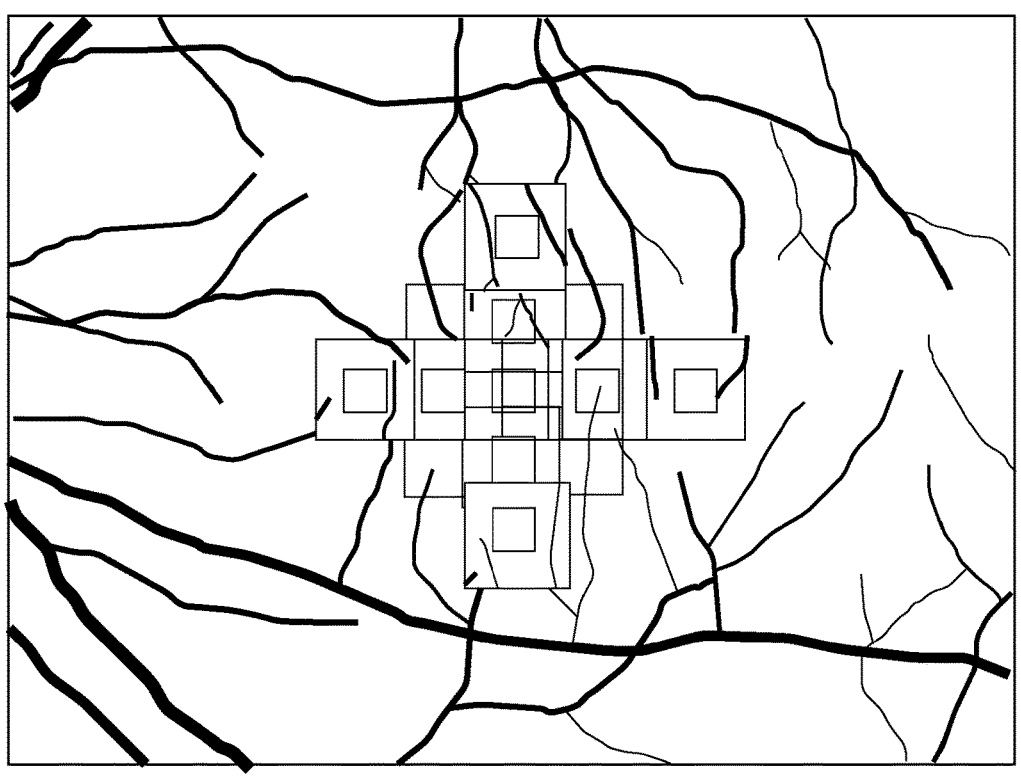
FIG. 3 is a schematic diagram illustrating an example of an AO-SLO image displayed on a WF-SLO image.
Figure 4:
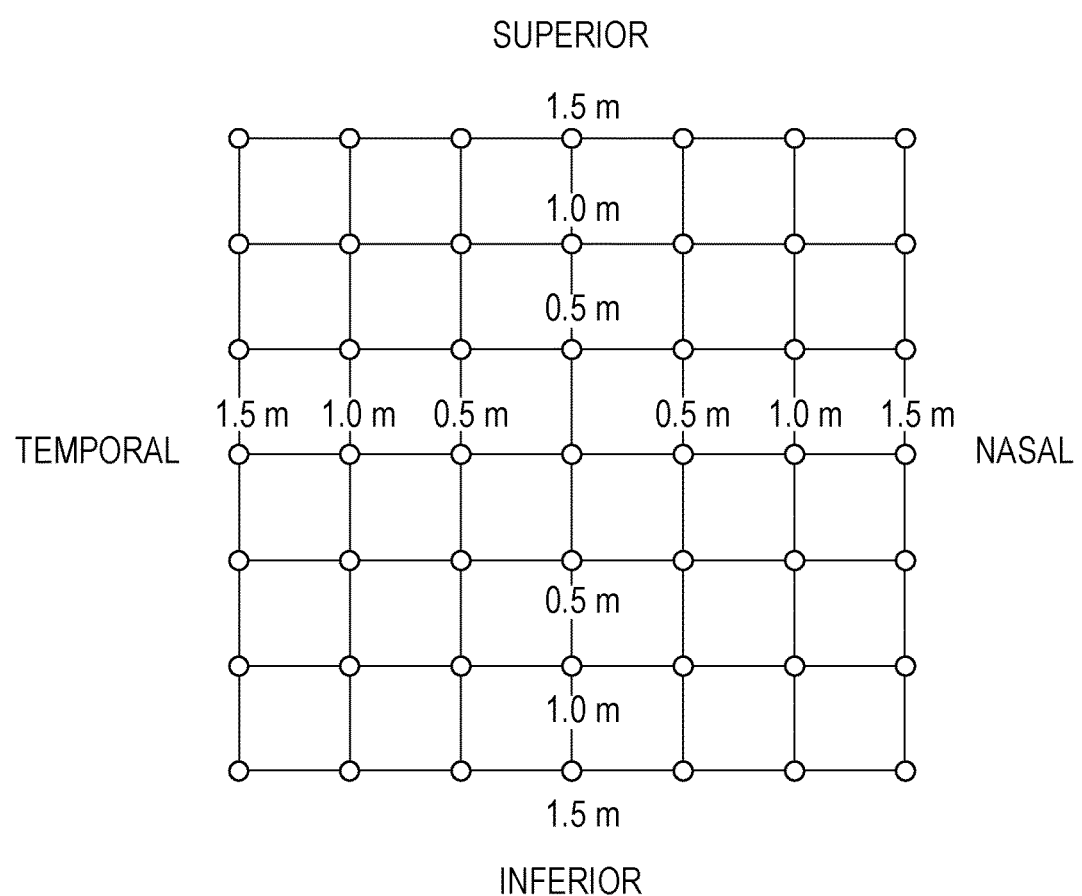
FIG. 4 is a schematic diagram illustrating an example of a fixation lamp map for designating a fixation position.

FIG. 3 schematically illustrates a plurality of AO-SLO images acquired by the AO-SLO apparatus according to this exemplary embodiment and a WF-SLO image. FIG. 3 illustrates an example of a state that AO-SLO images having a plurality of sizes are positioned on a WF-SLO image. It should be noted that the AO-SLO apparatus is capable of imaging the retina at different positions with a fixation lamp moved to different positions while the eye to be examined is gazing at different positions. FIG. 4 illustrates a fixation lamp map on which the presentation position of the fixation lamp may be operated.

For example, for the first imaging, the center of the fixation lamp map in FIG. 4 is kept selected, and the fixation lamp is presented. The position will be called a reference position below. In this case, imaging the eye to be examined gazing at the presented fixation lamp can result in imaging a region near the macula.

The WF-SLO image here refers to a low resolution image acquired without applying adaptive optics but acquired by imaging a wide range of the retina to capture the whole retina. By associating the AO-SLO images and the WF-SLO image, which position an AO-SLO image having a narrower field angle than that of the WF-SLO image exists on the WF-SLO image showing the whole retina. According to the following exemplary embodiments, the WF-SLO image has an image size of 8 mm×6 mm and a pixel size of 533×400. The AO-SLO images having three types of resolution exist which correspond to imaging regions having sizes of 1.7 mm×1.7 mm, 0.82 mm×0.82 mm, and 0.34 mm×0.34 mm and all having a pixel size of 400×400 in common. An AO-SLO image corresponding to an imaging region of 1.7 mm×1.7 mm will be called an L-image, and an AO-SLO image corresponding to an imaging region of 0.82 mm×0.82 mm will be called an M-image, and an AO-SLO image corresponding to an imaging region of 0.34 mm×0.34 mm will be called an S-image. In the following photoreceptor cell analysis, an S-image is mainly a subject of the analysis, but the present invention is not limited thereto. AO-SLO images having other sizes may be subjects of the photoreceptor cell analysis. It should be noted that each of the AO-SLO images and the WF-SLO image will also be called a planer image. The sizes of the planer images are not limited to the numerical values as described above but may be any other values.

Imaging Protocol

The imaging protocol of the eye to be examined may differ in accordance with the disease to be focused of the eye to be examined. In a normal protocol example, as illustrated in FIG. 3, a WF-SLO image having the macula at its center may be captured first. Then, a plurality of positions of the retina may be captured by combining AO-SLO images having different resolutions. It should be noted that the imaging time period and frame rate for the AO-SLO images may be changed. Here, as an example, the frame rate is equal to 32 frames per second, and the imaging time period is 32 images per second.

Processing to be Performed by Image Processing Device

Figure 2:
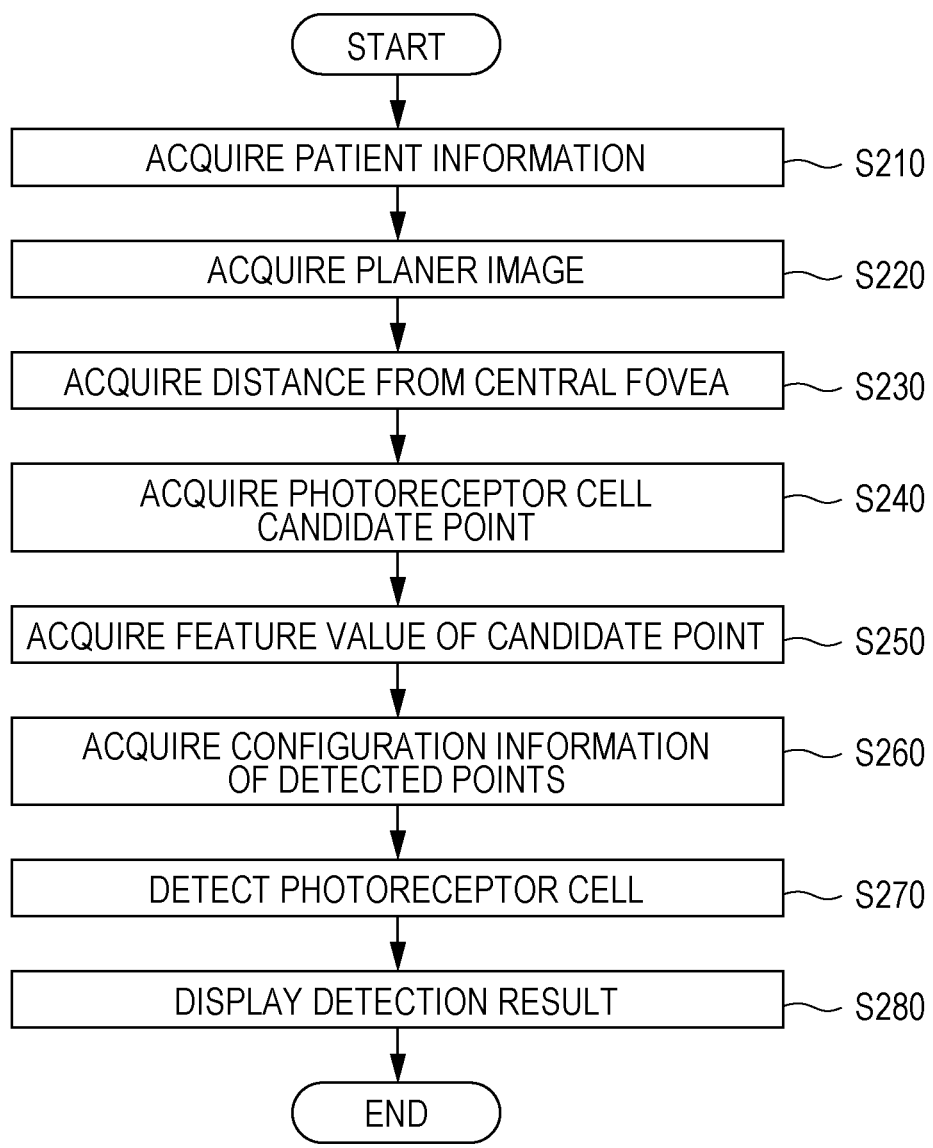
FIG. 2 is a flowchart illustrating an example of processing to be performed by the image processing device according to the first exemplary embodiment.

Next, processing to be performed by the image processing device 10 according to this embodiment will be described with reference to the flowchart in FIG. 2.

Step S210

In step S210, the information acquiring unit 110 acquires information regarding the eye to be examined from a database (DB), not illustrated. The information acquiring unit 110 then stores the acquired information regarding the eye to be examined in the storage unit 130 through the control unit 120. The information regarding the eye to be examined here may include patient information such as the ID and birthday of a patient, measurement data such as an axial length of the eye to be examined, and an image captured in the past.

Step S220

In step S220, the image acquiring unit 100 acquires planer images (WF-SLO image and AO-SLO images) of the retina of eye to be examined imaged by the AO-SLO apparatus. The planer images acquired by the image acquiring unit 100 are stored in the storage unit 130 through the control unit 120. It should be noted that the image acquiring unit 100 may directly acquire planer images from the AO-SLO apparatus or may acquire planer images stored in the DB, for example, from the DB, for example. The patient ID acquired in step S210, for example, may be used as a keyword for searching and acquiring planer images of the corresponding patient from the DB.

Step S230

In step S230, the positioning unit 141 positions the AO-SLO images and WF-SLO image acquired in step S220. Then, from the relationship between the position of the fovea designated on the WF-SLO image and the AO-SLO images positioned on the WF-SLO image, the distances from the fovea to the AO-SLO images is acquired.

A plurality of methods are available for designating the position of the fovea. For example, because the WF-SLO image is an image acquired by the fixation to the reference position, the center of the WF-SLO image may be defined as the fovea. Alternatively, the density of photoreceptor cells on the AO-SLO images positioned on the WF-SLO image and also acquired by fixation of the reference position may be evaluated, and the position having the highest density may be determined as the fovea. Further alternatively, the fovea may be defined from a run of the blood vessel near the macula.

The result of the association of the positions on the AO-SLO images and positions on the WF-SLO image and distances from the fovea to the AO-SLO images are stored in the storage unit 130 through the control unit 120.

Step S240

In step S240, the detecting unit 142 detects a point representing a candidate for a photoreceptor cell from the AO-SLO image to which the distance from the fovea is acquired in step S230.

A candidate point is detected by using the scheme, which will be described below. But a plurality of methods for the detection is known as in K. Y. Li and A. Roorda, "Automated identification of cone photoreceptors in adaptive optics retinal images," J. Opt. Soc. Am. A 24(5), 1358-1363 (2007) and is not limited to the scheme, which will be described below.

First, the detecting unit 142 overlays a subject AO-SLO image. Here, 32 frames of AO-SLO image exist for one imaging position, and one frame having the smallest distortion is selected and is defined as a reference frame. It should be noted that the number of frames is given for illustrative purpose only and is not limited to the value described above. The detecting unit 142 performs warping processing in which the remaining 31 frames are associated with the reference frame. The warping processing here applies a method including acquiring moving distances of images by applying phase only correlation to between the images and then dividing the images into 6×6 patches and acquiring an affine deformation amount between the images from the moving distances between the patches. It should be noted that the patch dividing method is not limited to 6×6 patches, but other values are also applicable. A different scheme may be used for the warping processing.

Next, for filtering processing, the detecting unit 142 applies an FFT low-pass filter to the acquired overlay image. It is known that the density of photoreceptor cells depends on the distances from the fovea, and a change resulting in a higher oscillation frequency than the frequency (oscillation frequency) corresponding to the highest density of photoreceptor cells is considered as noise which is then to be removed by the low-pass filter. In other words, the low-pass filter is a filter characterized in attenuating or cutting a higher frequency component than the frequency corresponding to the highest density of photoreceptor cells.

For detection processing, the detecting unit 142 detects a pixel where the brightness profile has a convex structure locally on the image having undergone the filtering processing. Adjacent pixels if detected are merged, and the center of gravity of the merged region is acquired to acquire a candidate point for a photoreceptor cell.

The detecting unit 142 stores the thus acquired position of the candidate point for a photoreceptor cell on the AO-SLO image in the storage unit 130 through the control unit 120.

Step S250

In step S250, the feature acquiring unit 143 calculates a feature value of the candidate point for a photoreceptor cell acquired in step S240. Various types of feature value may be considered, but a feature value based on a geometric shape of the brightness profile around the candidate point is focused here as an example. In other words, the feature acquiring unit 143 corresponds to an example of a second acquiring unit configured to acquire a second feature value different from the first feature value based on the brightness of the first candidate point.

More specifically, the feature acquiring unit 143 acquires a value acquired by applying a Laplacian of Gaussian (LoG) filter to the candidate point and/or a value acquired by applying a Hessian filter thereto. Here, σ of the applied Gaussian filter is changed, and σ resulting in a minimum value acquired by applying the LoG filter to candidate points and the corresponding LoG and Hessian then are acquired as the feature values. The feature acquiring unit 143 further acquires an average of brightness values of a total of five pixels including top and bottom and right and left four pixels with the candidate point as its center. It should be noted that the number of pixels is not limited to the top and bottom four pixels.

The feature acquiring unit 143 stores the thus acquired feature values of the candidate point for a photoreceptor cell on the AO-SLO image in the storage unit 130 through the control unit 120.

As described above, in step S250, feature values which correspond to the size and curvature of the candidate point are acquired from the pixel information of the region around the candidate point.

Step S260

In step S260, the configuration information acquiring unit 144 calculates a feature value in consideration of the configuration of the candidate point for a photoreceptor cell acquired in step S240. The feature value calculated in step S260 and the feature value calculated in step S250 may be called a first feature value and a second feature value, respectively.

Figure 5:
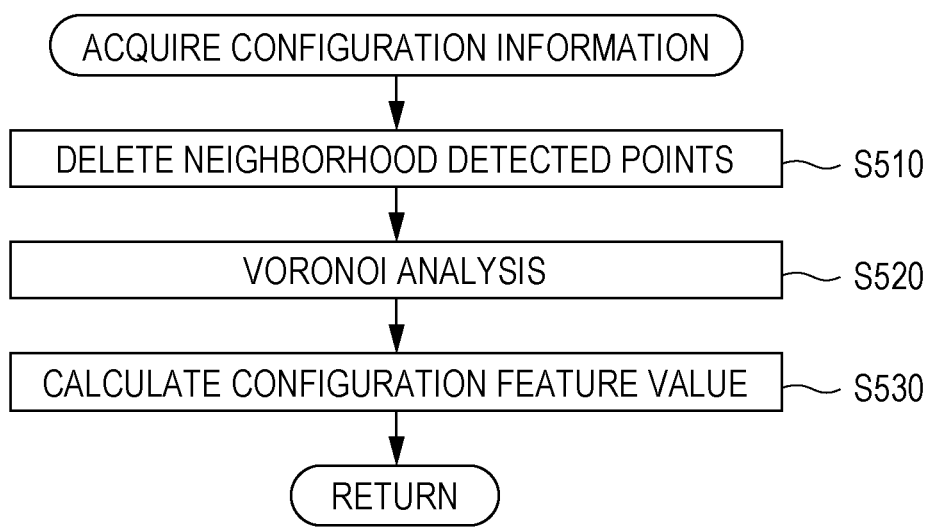
FIG. 5 is a flowchart illustrating a detail procedure of the configuration information acquisition in FIG. 2.

Detail processing of step S260 will be described with reference to FIG. 5.

Step S510

In step S510, the configuration information acquiring unit 144 removes a candidate point present at a position closer than the neighborhood of one candidate point from the candidate points for a photoreceptor cell acquired in step S240. The term "neighborhood" here refers to a distance (or region) based on a distance between photoreceptor cells assumed with respect to the distance from the fovea of the AO-SLO image. More specifically, the density D of photoreceptor cells and the distance $L_D$ between neighboring photoreceptor cells in a case where the photoreceptor cells are disposed in a honeycomb shape, which is considered as an ideal configuration, have the following relationship as in Expression (1).

$$D = \frac{2}{\sqrt{3} L_D^2} \quad (1)$$

Prior studies including anatomical data regarding the relationship between the distance from the fovea and the density of photoreceptor cells in a normal eye have been published. Thus, the configuration information acquiring unit 144 acquires an assumed density of photoreceptor cells from the distance from the fovea on an AO-SLO image with reference to the published values and calculates the distance $L_D$ between photoreceptor cells corresponding to the acquired density of photoreceptor cells. It should be noted that, the information describing a relationship between the photoreceptor cell density D and the distance $L_D$ between photoreceptor cells and information describing a relationship between a distance from the fovea and the photoreceptor cell density are pre-stored in a storage unit such as the storage unit 130.

According to this exemplary embodiment, the neighborhood is defined as $L_D*0.4$, and when one candidate point is neighboring to another candidate point in a distance shorter than the neighborhood, the configuration information acquiring unit 144 leaves the candidate point considered to be more likely a photoreceptor cell and deletes the other one from the candidate points. The definition of the neighborhood is not limited to the example above, but a factor to be multiplied by the distance $L_D$ may be a value other than 0.4, for example. The distance $L_D$ is a distance between photoreceptor cells in an ideal state, and the distance between photoreceptor cells of actually acquired photoreceptor cells may be shorter than the ideal distance due to irregularities of photoreceptor cells, for example. Even in this situation, when the neighborhood is defined as $L_D$ and when irregularities of photoreceptor cells exist, a candidate point which is actually a photoreceptor cell may be deleted. Accordingly, in this exemplary embodiment, $L_D$ is multiplied by a factor of 0.4 smaller than 1 so that a candidate point may be detected as a photoreceptor cell even when irregularities of photoreceptor cells exist. As described above, the factor to be multiplied by $L_D$ may be any value such as 0.5 if it is smaller than 1 for providing the effect. However, multiplying $L_D$ by an excessively smaller factor may result in deletion of the candidate point.

In order to evaluate the likelihood of a photoreceptor cell, a value acquired by applying the LoG filter acquired in step S250 is used. For example, when the values acquired by applying the LoG filter to two candidate points having a distance smaller than $L_D*0.4$ therebetween are equal to −250 and −600, respectively, the configuration information acquiring unit 144 deletes the former candidate point from the candidate points because the former candidate point has a convex structure smaller than that of the latter candidate point.

However, a plurality of evaluation methods are available, and, for example, one having a high brightness, one having a high α, or one having a shape close to a point shape as a result of Hessian filtering may be selected.

Step S520

Figure 6:
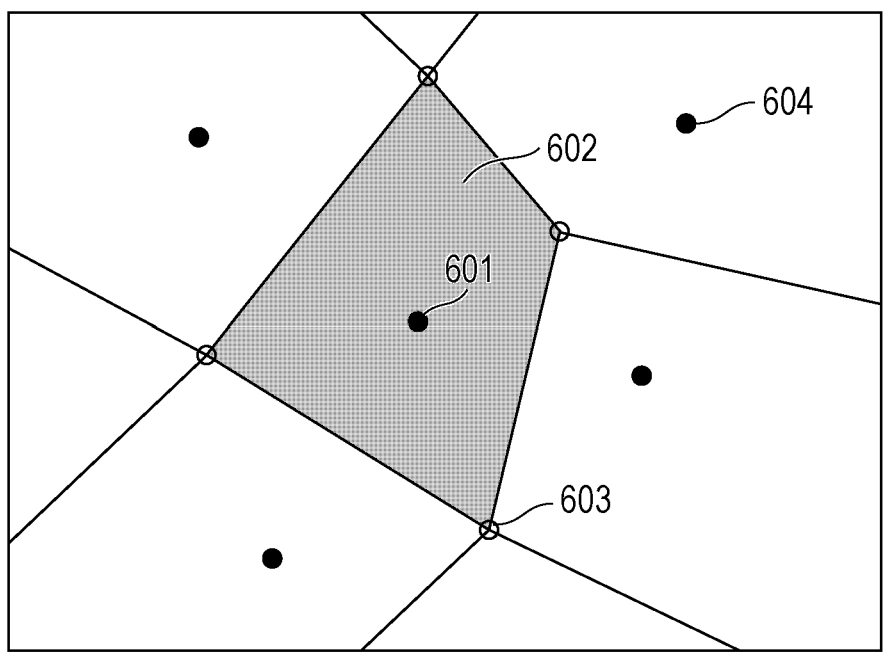
FIG. 6 is a schematic diagram illustrating an example of a voronoi analysis.

In step S520, the configuration information acquiring unit 144 performs a voronoi analysis on candidate points after the deletion of candidate points (hereinafter, also called a neighborhood removal) in step S510 is performed). The voronoi analysis refers to an analysis method which divides a region within an image by using a perpendicular bisector between two points with respect to a target set of points, as illustrated in FIG. 6. A region belonging to each detected point is called a voronoi region, the corresponding detected point is called a generating point, a detected point neighboring to the generating point is called a neighboring point, and a vertex of the voronoi region is called a voronoi point.

Step S530

In step S530, the configuration information acquiring unit 144 calculates a feature value of a candidate point in consideration of the configuration of the candidate point based on the voronoi analysis result acquired in step S520.

More specifically, feature values here are an average value $L_{ave}$ and a standard deviation K of the distance between a neighboring point and a generating point, which are acquired for each candidate point (generating point). The average value $L_{ave}$ corresponds to an example of an average value of distances between at least two or more candidate points including the first candidate point and the second candidate point among a plurality of candidate points.

It should be noted that a plurality of feature values based on a configuration exist and are not limited to exemplary ones here. For example, an oblate degree indicative of how much the voronoi region of each candidate point is close to a circle may be defined as a feature value. Furthermore, a feature value may be defined including not only a neighboring point of each candidate point but also a neighboring point of the neighboring point. A feature value based on a configuration may be defined without a voronoi analysis. More specifically, the number of points present within a radius $2*L_D$ from a candidate point may be defined as a feature value.

The configuration information acquiring unit 144 stores the feature values in consideration of the configuration between the thus acquired candidate points for a photoreceptor cell in the storage unit 130 through the control unit 120. The processing then returns to step S260.

Step S270

In step S270, the evaluating unit 145 acquires a detected point of a photoreceptor cell based on the feature values acquired in steps S250 and S260 from the candidate points for a photoreceptor cell acquired in step S240.

More specifically, the evaluating unit 145 determines whether the candidate point is a detected point (photoreceptor cell) or noise from the feature values acquired in steps S250 and S260.

The feature values acquired in step S250 is characterized as follows. For example, a candidate point having a higher brightness or a candidate point having a lower result of the LoG filter has a higher likelihood of a photoreceptor cell. One of Hessian eigen values X1 and X2 having a substantially equal value to that of the other one and having a higher absolute value than that of the other one has a higher likelihood of a photoreceptor cell. σ corresponding to the photoreceptor cell size assumed based on the distance from the fovea of the AO-SLO image has a higher likelihood of a photoreceptor cell. The evaluating unit 145 determines whether the candidate point is a detected point or noise in consideration of those described above.

Regarding the feature value based on the position of a candidate point acquired in step S260, an average value of the distance between a generating point and a neighboring point, which is close to the distance $L_D$ between photoreceptor cells acquired in step S510, has the generating point having a higher likelihood of a photoreceptor cell. A smaller dispersion of the distance between a generating point and a neighboring point has a higher likelihood of a photoreceptor cell.

There has been a plurality of known methods for identifying a photoreceptor cell based on a plurality of feature values. For example, one method includes learning by using data labeled as a photoreceptor cell or noise as a correct answer and determining an identification boundary. In this case, a discriminator such as a support vector machine and a neural network may be used.

An alternative method may weigh an effect of each feature value and define it as a score. As an example, a score S for a likelihood of a photoreceptor cell may be defined by Expression (2)

$$S = 0.8 * S_{LoG} + 0.2 * S_{voronoi} \tag{2}$$

where $$S_{LoG} = \begin{cases} 1.0 & (\text{if } LoG < -500) \\ -\dfrac{LoG}{500} & (\text{if } 0 > LoG > -500) \\ 0.0 & (\text{if } LoG > 0) \end{cases}$$

$$S_{voronoi} = \begin{cases} 1.0 - \left(\dfrac{L_{ave} - L_D}{L_D}\right)^2 & (\text{if } L_{ave} \leq 2*L_D) \\ 0 & (\text{if } L_{ave} > 2*L_D) \end{cases}$$

The evaluating unit 145 determines as a photoreceptor cell if the score S is higher than a certain threshold (such as 0.5) as noise if it is equal to or lower than the threshold. The threshold may be a value other than 0.5. It should be noted that, for calculation of the score S, $S_{LoG}$ is a value acquired by applying the LoG, and $S_{voronoi}$ is a value acquired based on the distance between candidate points. More specifically, $S_{voronoi}$ is acquired based on the average value $L_{ave}$ of the distance between a neighboring point and a generating point and the distance $L_D$ between photoreceptor cells having an ideal state. The distance $L_D$ between photoreceptor cells is a value that varies based on the distance from the fovea in an SAO-SLO image from which a photoreceptor cell is to be detected. In other words, $S_{voronoi}$ corresponds to an example of the first feature value acquired based on the distance between the position and the fovea in the eye fundus of the eye to be examined from which the eye fundus image is acquired and the distance between the first candidate point and the second candidate point. The distance $L_D$ between photoreceptor cells corresponds to an example of a reference distance between photoreceptor cells acquired based on the distance between the position and the fovea in the eye fundus of the eye to be examined from which the eye fundus image is acquired. In other words, the first feature value is acquired based on the reference distance and the distance between the first candidate point and the second candidate point.

Furthermore, in the expression above, $S_{voronoi}$ is acquired by dividing the difference between the average value $L_{ave}$ of the distances each between a neighboring point and a generating point and the distance $L_D$ between photoreceptor cells to be referred by the distance $L_D$ between photoreceptor cells. In other words, the first feature value is acquired based on the difference between the distance between the first candidate point and the second candidate point and the reference distance. As the difference between the average value $L_{ave}$ and the distance $L_D$ between photoreceptor cells to be referred decreases, $S_{voronoi}$ increases, facilitating the determination that the candidate point is a photoreceptor cell. In other words, $S_{voronoi}$ corresponding to an example of the first feature value changes to the value representing the probability that the first candidate point is a photoreceptor cell, by the determining unit, as the difference between the average value $L_{ave}$ and the distance $L_D$ between photoreceptor cells decreases.

Having described that the factor for $S_{LoG}$ is 0.8 and that the factor for $S_{voronoi}$ is 0.2, the factors are not limited to those values and may be other values.

Alternatively, a feature value acquired from a local region around a candidate point and a feature value based on the configuration of candidate points may be used for playing different roles. More specifically, a method may be used which determines the score for the likelihood of a photoreceptor cell is determined only from the feature value acquired from a local region and changes the magnitude of the threshold in accordance with the feature value based on the position of the candidate point. More specifically, a score defined by Expression (3) is considered.

$$S = 0.8 * S_{LoG} + 0.2 * S_{size} \quad (3)$$

where $$S_{size} = 1.0 - \frac{\max(0, \sigma_{ideal} - \sigma)}{\sigma_{ideal}}$$

A low score is obtained only when σ is lower than an ideal value $\sigma_{ideal}$ of σ that varies in accordance with the distance from the fovea. A lower σ used for photoreceptor cell detection than the ideal value $\sigma_{ideal}$ means that the distance between candidate points is shorter than the ideal distance. In other words, it means that there is a possibility that noise is detected as a candidate for a photoreceptor cell. The ideal value $\sigma_{ideal}$ of σ is defined by using Expression (4).

$$\sigma_{ideal} = \begin{cases} \sigma & (d \leq 1.0) \\ d & (1.0 < d \leq 2.0) \\ 2.0 & (2.0 < d) \end{cases} \quad (4)$$

where d is a distance from the fovea.

The threshold T to be used for determining whether the candidate point is a photoreceptor cell or not is defined by using Expression (5).

$$T = \begin{cases} 0.3 & (\text{if } L_{ave} > L_D \text{ and } K < 0.3 * L_D) \\ 0.5 & (\text{else}) \end{cases} \quad (5)$$

The evaluating unit 145 determines that the candidate point is a photoreceptor cell if the score S of each of the detected points is higher than T and determines it as noise if the score S is equal to or lower than the threshold T. It should be noted that values such as 0.3 and 0.5 used for the determination of the value of the threshold T are given for illustrative purpose only and are not limited to those values. It should be noted that the values such as 1.0 and 2.0 used for determining the ideal value $\sigma_{ideal}$ are given for illustrative purpose and are not limited to those values.

The evaluating unit 145 stores the detected points of a photoreceptor cell on the AO-SLO image acquired as described above and the corresponding scores in the storage unit 130 through the control unit 120.

Step S280

In step S280, the output unit 150 acquires the AO-SLO image acquired in step S220 and the detected points of a photoreceptor cell acquired in step S270 from the storage unit 130 through the control unit 120. The output unit 150 then displays and presents the detected points over the AO-SLO image on an external monitor, not illustrated, for example, to a user and at the same time store them in a DB, not illustrated, for example.

As described above, a detected point determined as a photoreceptor cell is selected based on feature values acquired from the AO-SLO image from candidate points and a positional relationship (configuration) between the candidate points. Thus, according to this embodiment, the photoreceptor cell detection with higher accuracy may be implemented compared with a conventional technology not in consideration of the positional relationship between candidate points.

More specifically, because the brightness of a photoreceptor cell changes with time, even a photoreceptor cell may have a low brightness at some point of imaging time. According to the present invention in consideration of not only the brightness but also the position of a photoreceptor cell, a failure of detection of a photoreceptor cell due to some imaging times may be prevented.

Also when noise causes an actual photoreceptor cell to have a lower brightness on an AO-SLO image, the photoreceptor cell may be detected with high accuracy because this exemplary embodiment considers the configuration of the photoreceptor cell.

Having described that a voronoi analysis is performed according this exemplary embodiment, step S530 may be executed without a voronoi analysis. In other words, a voronoi analysis is not a required process (and the same is true for the following exemplary embodiments). This means that one candidate point may be defined as a generating point (reference point), and a point neighboring thereto may be extracted. Because performing a voronoi analysis clarifies a voronoi region neighboring to a voronoi region containing a generating point, candidate points contained in the neighboring voronoi region may be referred to find a neighboring candidate point. Thus, performing the processing in step S530 after performing a voronoi analysis can provide an effect that facilitates the processing using a candidate point neighboring to a generating point.

Having described that whether a candidate point is a photoreceptor cell or not is determined based on $S_{LoG}$ and $S_{voronoi}$ in step S530, an embodiment of the present invention is not limited thereto. $S_{LoG}$ may not be used but $S_{voronoi}$ may be used to determine whether a candidate point is a photoreceptor cell or not.

Second Exemplary Embodiment

According to the first exemplary embodiment, both of the feature value based on the position of a candidate point and the feature value acquired from an AO-SLO image are used to detect a photoreceptor cell.

According to a second exemplary embodiment on the other hand, the photoreceptor cell detection may be performed based on only the feature value acquired from an AO-SLO image, and the photoreceptor cell detection is performed again on candidate points determined as not being a photoreceptor cell based on the feature values of their positions.

Because the functional configuration of the image processing device 10 according to this exemplary embodiment is the same as that illustrated in FIG. 1, the repetitive description will be omitted.

Figure 7:
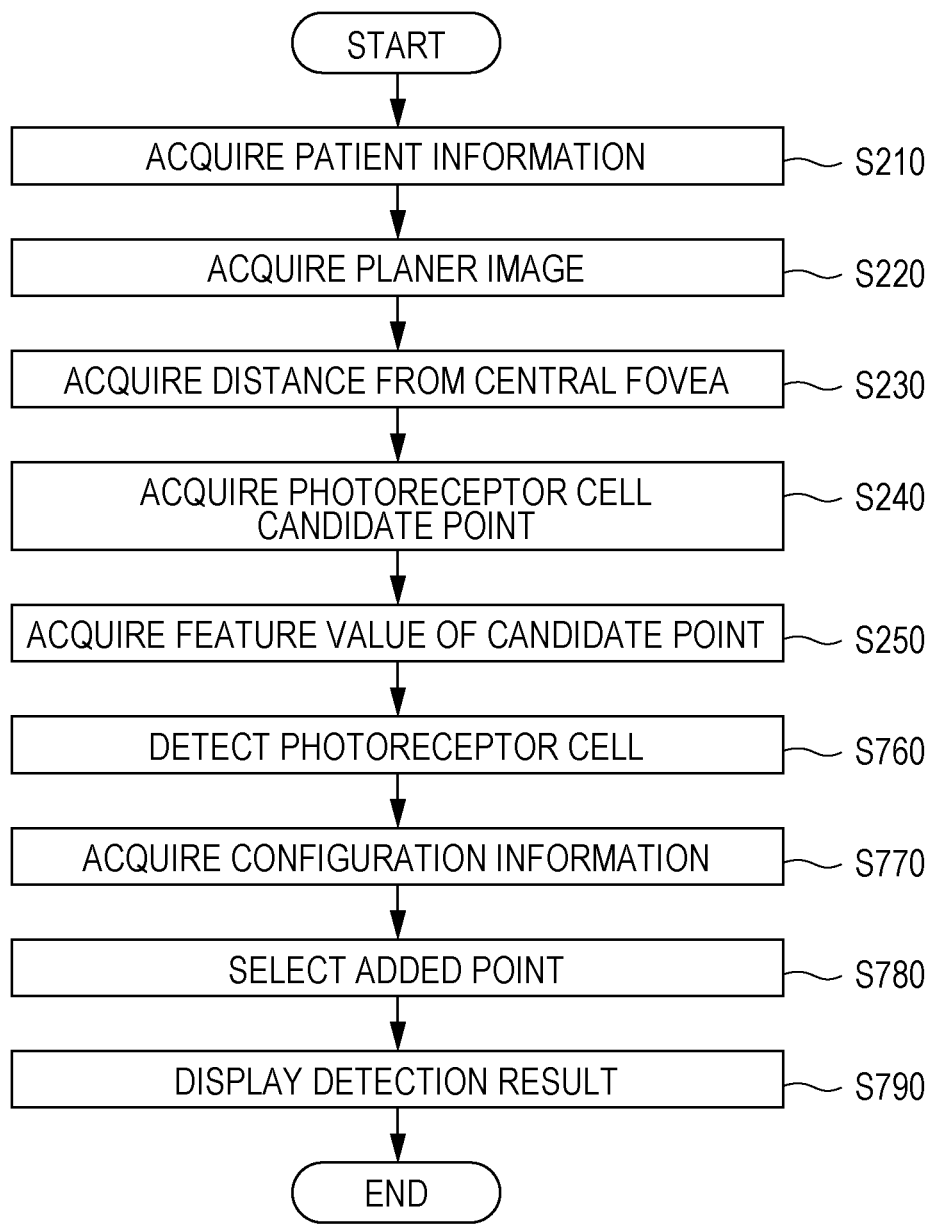
FIG. 7 is a flowchart illustrating an example of a procedure to be performed by an image processing device according to a second exemplary embodiment.

With reference to the flowchart in FIG. 7, the processing procedure of the image processing device 10 according to this embodiment will be described. Because the procedure in step S210 to S250 is the same as that in the first exemplary embodiment, the repetitive description will be omitted.

Step S760

In step S760, the evaluating unit 145 determines whether a candidate point for a photoreceptor cell acquired in step S240 is a point representing a photoreceptor cell or not based on the feature value acquired in step S250. The feature acquiring unit 143 in step S250 corresponds to an example of a second acquiring unit configured to acquire a second feature value different from the first feature value from the first candidate point and the second candidate point.

In this case, a score is defined only based on the feature value acquired from an AO-SLO image and determines whether the candidate point is a photoreceptor cell or not in accordance with a comparison result between the score and the threshold. More specifically, the score is defined by using Expression (6) as in the second half of the description regarding step S270 above.

$$S=0.8*S_{LoG}+0.2*S_{size} \quad (6)$$

Assume that the threshold to be used for the determination of whether the candidate point is a photoreceptor cell or not is 0.5 for all detected points. The evaluating unit 145 determines that the detected point of interest is a photoreceptor cell if the score of the detected point is higher than 0.5 and as noise if it is equal to or lower than 0.5. It should be noted that the threshold may be any other value though it is 0.5 in this embodiment.

The evaluating unit 145 stores the thus acquired detected points for photoreceptor cells on the AO-SLO image and a candidate points determined as noise (hereinafter, each also called a noise point) in the storage unit 130 through the control unit 120.

Step S770

In step S770, the evaluating unit 145 acquires the detected points for photoreceptor cells acquired in step S760 and noise points and acquires configuration information on the noise points with respect to the photoreceptor cell detected points.

Figure 8:
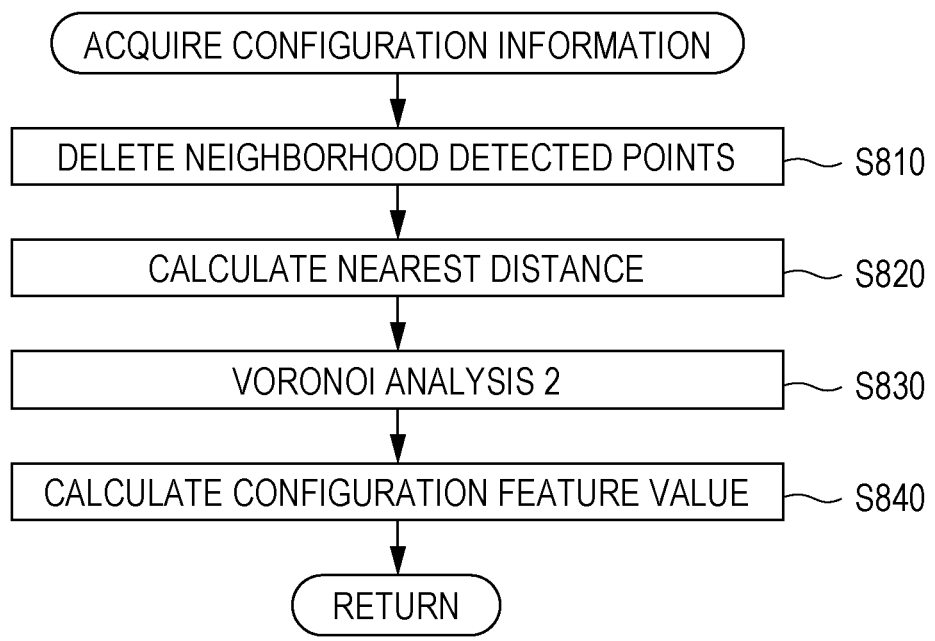
FIG. 8 is a flowchart illustrating an example of a detail procedure of the configuration information acquisition in FIG. 7.

With reference to FIG. 8, the processing in step S770 will be described in more detail.

Step S810

In step S810, the configuration information acquiring unit 144 removes a noise point present at a closer position than the neighborhood of one noise point from the noise points acquired in step S770 in the same manner as in step S510. Hereinafter, a noise point after the neighborhood point is removed will be called a second candidate point. The definition for the term "neighborhood" is the same as in the first exemplary embodiment.

Step S820

In step S820, the configuration information acquiring unit 144 acquires a nearest neighbor distance between photoreceptor cell detected points (hereinafter, each also called a first photoreceptor cell detected point) acquired in step S760.

More specifically, a voronoi analysis is performed on the first photoreceptor cell detected points in the same manner as in step S520. Then, a neighboring point at the shortest distance from a generating point is selected from the neighboring points corresponding to the first photoreceptor cell detected points (generating points), and the distance is defined as a nearest neighbor distance (NND) of each of the generating points. Next, the configuration information acquiring unit 144 acquires a distribution of the NNDs of all first photoreceptor cell detected points. When there is a region where the photoreceptor cell detection has not been performed correctly, the NNDs of the surrounding detected points increase. When noise is improperly detected, the NNDs of the surrounding detected points decrease. In order to remove the effect of such incomplete detections, the configuration information acquiring unit 144 acquires a frequency distribution of NNDs of all of the first photoreceptor cell detected points and then acquires a most frequent NND (MFNND below). For the acquisition of such a frequency distribution, the size of a bin used for a histogram is important. The size of the bin is equal to 0.2 μm here, but the value depends on the pixel resolution of the subject image and is not limited to 0.2 μm.

Step S830

In step S830, the configuration information acquiring unit 144 performs a voronoi analysis on points including the second candidate points acquired in step S810 and the first photoreceptor cell detected points acquired in step S760 in the same manner as in step S520.

A voronoi analysis is performed on all candidate points in step S520 while, according to this embodiment, positions of the first photoreceptor cell detected points around the second candidate points are evaluated, which is a difference. In other words, the configuration information acquiring unit 144 handles a generating point as the second candidate point and a neighboring point as the first photoreceptor cell detected point.

Step S840

In step S840, the configuration information acquiring unit 144 calculates a feature value based on the configuration from the result of the voronoi analysis performed on each of the second candidate points acquired in step S830 in the same manner as in step S530.

More specifically, the average value $L_{ave}$, dispersion K, and NNDs of the distances between the neighboring points (first photoreceptor cell detected points) and a generating point acquired with respect to a candidate point (generating point: second candidate point) are handled as feature values.

However, a plurality of feature values based on a configuration is available and is not limited to those in this embodiment.

The thus acquired feature values based on the MFNND with respect to the first photoreceptor cell detected points and the positions of the second candidate points are stored in the storage unit 130 through the control unit 120, and the processing then returns to step S770. The MFNND with respect to the first photoreceptor cell detected points is a value acquired by performing the analysis on the first photoreceptor cell detected point other than noise points in step S820. The feature value based on the configuration of the second candidate points is a value acquired by performing the analysis on the noise points and the first photoreceptor cell detected points in step S820.

Step S780

In step S780, the evaluating unit 145 selects points to be detected as photoreceptor cells from the second candidate points based on the MFNND acquired in step S820 and the feature value of the second candidate points acquired in step S840.

Each of the points to be selected here is positioned at a distance approximately 1.0 to 3.0 times of MFNND from the first photoreceptor cell detected points among the second candidate points and has a score closer to the threshold. Though each of such second candidate points has been determined in step S760 as not being a photoreceptor cell due to an effect of blinking of the brightness inherent to photoreceptor cells and noise occurring during imaging, but there are a high possibility that they are photoreceptor cells in consideration of the positional relationships between candidate points.

More specifically, points having the following features (hereinafter, called "selected second candidate points") are selected from the second candidate points.

$$0.4*L_D < NND,$$

$$MFNND < L_{ave} < 3*MFNND,$$

$$K < 0.3*L_D,$$

In this case, the determination conditions include that the NND acquired in step S840 is higher than $0.4*L_D$ and that the average value $L_{ave}$ of distances between the second candidate points and the first photoreceptor cell detected points acquired in step S840 is higher than the MFNND acquired in step S820 and is lower than 0.3*MFNND. The determination conditions may further include that dispersion L of the distances between the second candidate points and the first photoreceptor cell detected points is lower than $0.3*L_D$. The determination condition that the NND acquired in step S840 is higher than $0.4*L_D$ is used in consideration of the fact that the photoreceptor cells are not positioned ideally. In other words, $L_D$ is multiplied by a factor lower than 1. However, multiplying $L_D$ by an excessively low factor results in determination that the second candidate point is possibly a photoreceptor cell when the NND is excessively low (when the second candidate point is apparently noise). According to this exemplary embodiment, $L_D$ is multiplied by the factor equal to the value above. The criterion formula for the average value $L_{ave}$ determines the factor to be multiplied by MFNND in consideration of that, because the MFNND acquired in step S820 is the most frequent NND, the NNDs acquired in step S820 includes an NND higher than the MFNND.

The criterion formula for the dispersion K determines the factor to be multiplied by $L_D$ in consideration of that photoreceptor cells are not arranged at ideal positions and that a second candidate point excessively close to a first photoreceptor cell detected point is required to be processed as noise.

It should be noted that the factor is not limited to the example above but may be any of other values. For example, the factor to be multiplied by MFNND may be a value lower than 1 instead of 1.

Having described that three conditions are used for determining whether a second candidate point is a photoreceptor cell or not, an embodiment of the present invention is not limited thereto.

The evaluating unit 145 may select one having a score, which is defined in step S760, equal to or higher than 0.3 as an additional detected point (hereinafter, called a second photoreceptor cell detected point). Having described that according to this exemplary embodiment, the threshold is 0.3, an embodiment of the present invention is not limited thereto.

The evaluating unit 145 stores the thus acquired second photoreceptor cell detected point in the storage unit 130 through the control unit 120.

As described above, even when a candidate point is determined as noise in step S760, the configuration information acquiring unit 144 in step S840 calculates a distance between a candidate point determined as being noise and a candidate point determined as being not noise. In step S780 then, the evaluating unit 145 determines whether the candidate point determined as being noise once is really noise or not again based on the calculated distance. In other words, when the determining unit determines based on the second feature value that the first candidate point is not a point representing a photoreceptor cell and the second candidate point is a point representing the photoreceptor cell, the determining unit determines whether the first candidate point is a point representing a photoreceptor cell or not based on the first feature value.

Step S790

In step S790, the output unit 150 acquires from the storage unit 130 through the control unit 120 the AO-SLO image acquired in step S220, the first photoreceptor cell detected point acquired in step S760, and the second photoreceptor cell detected point acquired in step S780. Then, the detected points are displayed over the AO-SLO image on an external monitor, not illustrated, and are stored in a DB, not illustrated.

In this case, the output unit 150 may use different colors for displaying the first photoreceptor cell detected points and the second photoreceptor cell detected points so that a user can clearly distinguish them. From this, a user can recognize a point which is indicated as being highly possibly noise based on features of the AO-SLO image but as being possibly a photoreceptor cell based on the state of the configuration of detected points and can manually modify the point especially with care. In other words, when the determining unit determines that the first candidate point is a point representing the photoreceptor cell based on the first feature value, the output unit 150 corresponds to an example of a display control unit configured to display the first candidate point and the second candidate point in different display forms.

Having described above the case where the threshold is defined in step S780 to confirm the second photoreceptor cell detected point, the second candidate point selected and its score may be stored in step S780, and a threshold may be defined based on an input from a user in step S790 for display.

More specifically, a slider bar may be provided to allow a change of the threshold. Only the second candidate point having a score equal to or higher than the threshold may be displayed along with the first photoreceptor cell detected points in different colors. This type of display may support the user's manual modification more efficiently. According to this exemplary embodiment, the accuracy of the photoreceptor cell detection may be improved like the first exemplary embodiment.

More specifically, because the brightness of a photoreceptor cell changes with time, even a photoreceptor cell may have a low brightness at some point of imaging time. According to the present invention in consideration of not only the brightness but also the position of a photoreceptor cell, a failure of detection of a photoreceptor cell due to some imaging times may be prevented.

Also when noise causes an actual photoreceptor cell to have a lower brightness on an AO-SLO image, the photoreceptor cell may be detected with high accuracy because this exemplary embodiment considers the position of the photoreceptor cell.

Third Exemplary Embodiment

According to the second exemplary embodiment, a point present at a position where a photoreceptor cell may possibly be present is selected again based on configuration information from candidate points determined as being noise. According to a third exemplary embodiment, whether a candidate point determined as being noise exist or not, a detected point which has been highly possibly detected improperly is removed based on configuration information, and a detected point is set at a position where a photoreceptor cell possibly exists.

Because the functional configuration of the image processing device 10 according to this exemplary embodiment is the same as the one illustrated in FIG. 1, the repetitive description will be omitted.

Figure 9:
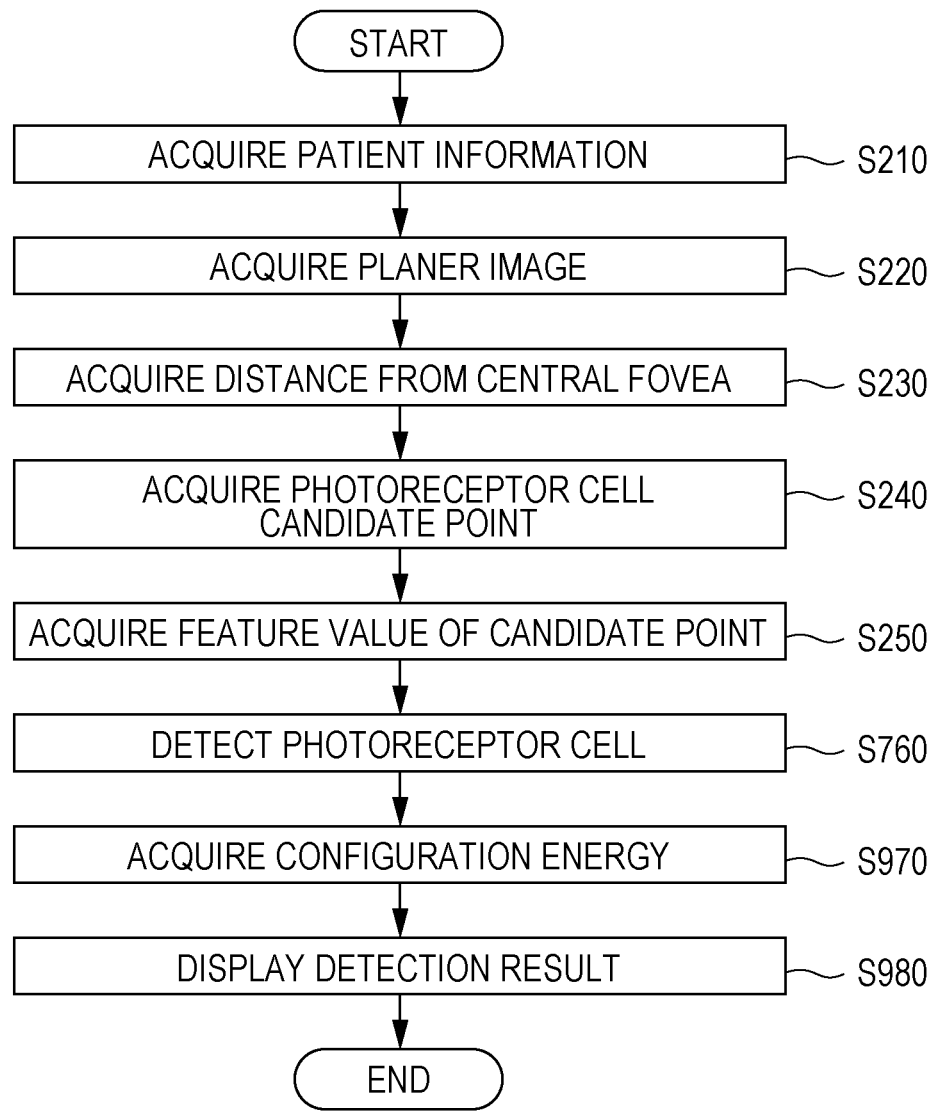
FIG. 9 is a flowchart illustrating an example of a procedure to be performed by an image processing device according to a third exemplary embodiment.

With reference to FIG. 9, a processing procedure to be performed by the image processing device 10 according to this embodiment will be described. Because the processing procedure in step S210 to S250 is the same as the processing procedure according to the first exemplary embodiment and processing procedure in the step S760 is the same as the processing procedure according to the second exemplary embodiment, the repetitive description will be omitted.

Step S970

Figure 10:
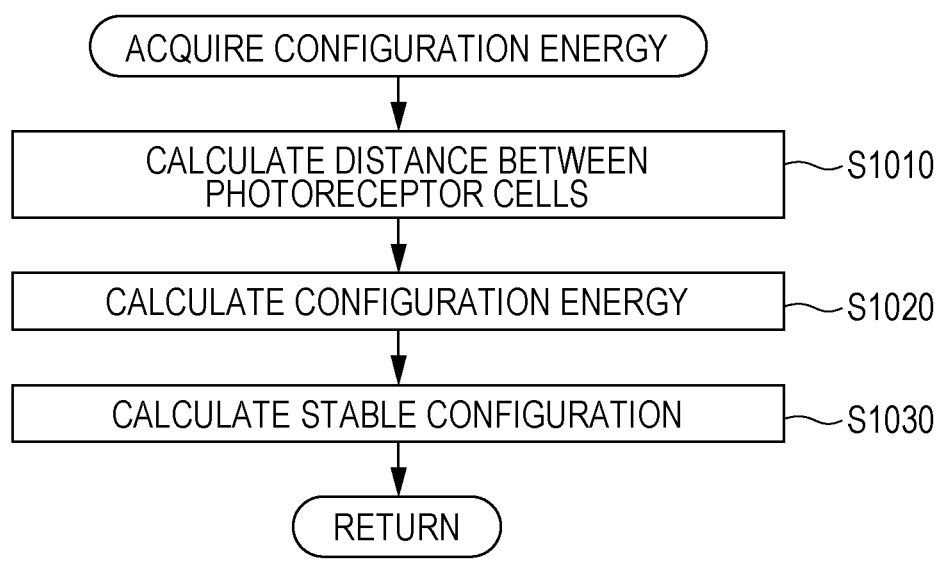
FIG. 10 is a flowchart illustrating an example of a detail procedure of the position power acquisition in FIG. 9.

In step S970, the configuration information acquiring unit 144 acquires a photoreceptor cell detected point (first photoreceptor cell detected point) acquired in step S760 and calculates configuration energy from the configuration state. With reference to FIG. 10, further detail steps will be described. FIG. 6 illustrates a result of a voronoi analysis and illustrates a generating point 601, a voronoi region 602, a voronoi point 603, and a neighboring point 604.

Step S1010

In step S1010, the configuration information acquiring unit 144 acquires an average distance between first photoreceptor cell detected points acquired in step S760. More specifically, a voronoi analysis is performed on first photoreceptor cell detected points to acquire a distribution of distances between all generating points and neighboring points, and a most frequent distance is defined as an average distance. In this case, because the first photoreceptor cell detected points includes false positive and false negative points such as noise and non-detected points, the acquired distances between generating points and neighboring points may include incorrect values. However, it may be considered that the acquisition of a most frequent distance may contribute to the acquisition of a more correct value. The most frequent distance in the distribution of distances between the all generating points and neighboring points acquired here will be called a neighboring average distance $L_N$, hereinafter.

Step S1020

In step S1020, the configuration information acquiring unit 144 acquires the average distance and a voronoi analysis result between the first photoreceptor cell detected points acquired in step S1010 and calculates configuration energy of the first photoreceptor cell detected points.

More specifically, the configuration energy of each of the first photoreceptor cell detected point n is defined by using Expression (6).

$$E_n = \frac{1}{2N_n} \sum_{j=1}^{N_n} (L_j - L_N)^2 + \lambda \Delta \mu \qquad (6)$$

In this case, $N_n$ is the number of neighboring points corresponding to the first photoreceptor cell detected points (generating points n), and $L_j$ is a distance between the generating points and the corresponding neighboring points. $\Delta \mu$ corresponds to potential energy when one photoreceptor cell exists and, by using the average brightness value $I_{Ave}$ of the whole AO-SLO image and the brightness value I of a detected point, is defined by using Expression (7).

$$\Delta \mu = \frac{(I_{ave} - I)}{I_{ave}} \qquad (7)$$

λ is a parameter that determines the balance between a first term dependent on the mutual configuration of detected points and a second term representing potential energy of a single detected point.

The potential energy may be defined in a plurality of ways. For example, though the average brightness value $I_{Ave}$ of the whole AO-SLO image is used, an average of brightness values of the first photoreceptor cell detected points may be used, or an average of brightness values of all photoreceptor cell candidate points acquired in step S230.

Assuming the number of the first photoreceptor cell detected points is equal to N, the entire configuration energy $E_{configuration}$ is defined by using Expression (8) by integrating the energies of the first photoreceptor cell detected points.

$$E_{Layout} = \sum_{n=1}^{N} E_n \qquad (8)$$

Step S1030

In step S1030, the configuration information acquiring unit 144 acquires a configuration of photoreceptor cells which minimizes the configuration energy acquired in step S1020.

In this case, detected points are added or deleted without searching positions of the first photoreceptor cell detected points.

First, a point having a low NND (generating point m) is focused among the first photoreceptor cell detected points acquired in step S1020. The deletion of points affects the entire configuration energy and reduces the configuration energy $E_m$ of the generating point m and at the same time affects the change in shape of the voronoi region having all neighboring point $(1 \subset N_m)$ of m as generating points.

$$\Delta E_{Layout} = -E_m + \sum_{l \in V_m} \Delta E_l \quad (9)$$

Therefore, a voronoi analysis is performed again on all neighboring points of m, and a difference in energy before and after the voronoi analysis is acquired.

This processing is performed on all first photoreceptor cell detected points having an NND lower than $0.5^*L_D$. If the whole configuration energy is reduced, the point is defined as deletion candidate points for reducing the whole configuration energy. It should be noted that the factor to be multiplied by $L_D$ may be any of other values.

Next, a point having a farthest neighbor distance (FND) is focused among the first photoreceptor cell detected points acquired in step S930. The FND refers to a distance between neighboring points at a longest distance from a generating point among neighboring points corresponding to generating point, in the same way of thinking as NND. In order to reduce the energy of a detected point, another detected point may be added closely to the middle point between the detected point and the neighboring point being FND. Therefore, when the magnitude of FND is two or more times of $L_N$, the configuration information acquiring unit 144 defines added point energy $\Delta E_{ADD}$ about the middle point $x_A$ between the generating point and the neighboring point being FND. In other words, the configuration information acquiring unit 144 corresponds to an example of an adding unit configured to add a candidate point based on the distance between a first candidate point and a second candidate point.

$$\Delta E_{ADD} = f(x_a) \quad (10)$$

In this case, the function f may be Gaussian about $x_A$. More simply, the function f may be a value corresponding to the inverse number of the distance by limiting to the range appropriately two times of $L_N$.

Then, added point energies of all first photoreceptor cell detected points contributing to an FND having a magnitude equal to or larger than two times of $L_N$ are added up.

$$E_{ADD} = \sum_{n=1}^{N} \Delta E_{m,ADD} \quad (11)$$

With respect to a point where a photoreceptor cell should actually be detected but is determined as being false negative, the added point energies of a plurality of detected points surrounding the point are added up so that the point has a clearly small energy. Some methods are available for the selection of a candidate point to be added. For example, a minimum value of $E_{ADD}$ of a point may be acquired, and if it is equal to or lower than a certain threshold, the point is selected as the addition candidate point. Alternatively, like the selection of a deletion candidate point, a change $\Delta E_{configuration}$ of the configuration energy is calculated from a change of the voronoi region of the first photoreceptor cell detected points surrounding an addition candidate point if added. If the whole configuration energy is reduced, the point is defined as an addition candidate point.

The thus acquired deletion candidate points and addition candidate points are stored in the storage unit 130 through the control unit 120, and the processing returns to step S970.

Step S980

In step S980, the output unit 150 acquires from the storage unit 130 through the control unit 120 the AO-SLO image acquired in step S220, photoreceptor cell detected points (first photoreceptor cell detected points) acquired in step S760, the deletion candidate points and addition candidate points acquired in step S970. The acquired points over the AO-SLO image are displayed on an external monitor, not illustrated, and are stored in a DB, not illustrated.

In this case, the color of the deletion candidate points and addition candidate points may be different from the color of the first photoreceptor cell detected points so that a user can clearly distinguish them. From this, a user can recognize a point which is possibly noise based on the regular configuration of photoreceptor cells and a point which is indicated as being possibly noise against detected points acquired based on a local feature of the image and can manually modify the point especially with care.

The deletion candidate points may be deleted from the first photoreceptor cell detected point in advance and may not be presented to a user or may be presented to a user as deletion candidate points and may be deleted from the first photoreceptor cell detected point after a user checks them.

Having described that the addition candidate points are confirmed with reference to the threshold defined in step S970 for an addition candidate point, a minimum points of $E_{ADD}$ and the values are stored in step S970, and an addition candidate point may be displayed with reference to a threshold defined by a user input in step S980. More specifically, a slider bar may be provided to allow a change of the threshold. Only the minimum points having $E_{ADD}$ values equal to or lower than the threshold may be displayed in a different color. This type of display may support the user's manual modification more efficiently.

Having described that deletion candidate points and addition candidate points are acquired and are presented in step S970, an analysis result of the configuration energy in step S970 may be presented to a user.

For example, a distribution of added point energies $E_{ADD}$ may be acquired as an image. Furthermore, the amount of change $\Delta E_{configuration}$ of the configuration energy when a generating point m is deleted, which is calculated when a deletion candidate point is selected and is acquired for a generating point m having an NND, is imaged. More specifically, a Gaussian having a magnitude of $\Delta E_{configuration}$ is placed at the center of the position of the generating point m and is integrated for all deletion candidate points. By integrating the distribution intensity of the added point energy $E_{ADD}$ in blue and the integrated image $\Delta E_{configuration}$ in red, a region having a first photoreceptor cell detected point being high possibly false positive may be displayed in red and a region having a first photoreceptor cell detected point being highly possibly false negative in blue. It may be considered that this kind of distribution of possibilities of being false positive and false negative of detection results may exhibit the reliability of the detection result. This reliability distribution may be presented to a user so as to support the user's manual modification more efficiently.

Fourth Exemplary Embodiment

Having described that, according to the first to third exemplary embodiments, photoreceptor cells are present in a detection subject region, for example. However, there may be a case where a region without photoreceptor cells may spread within an image due to the existence of a blood vessel structure and a disease, for example. In such a case, a region other than the detection subject may be masked, and the processing may be performed on the region other than the masked region.

Such a mask is generated between steps S230 and S240 according to any one of the first to third exemplary embodiments. Assuming that the mask generation is performed in step S235, details thereof will be described below.

Step S235

In step S235, the detecting unit 142 acquires a region in which a photoreceptor cell is not rendered as a mask region from the AO-SLO image acquired in step S220.

Such a region in which a photoreceptor cell is not rendered may possibly have a blood vessel, for example. A photoreceptor cell is not easily clearly rendered because of an effect of incident light weaken by a blood vessel prevent in an upper layer (close to the vitreous body of the retina). In this case, the accuracy of detection decreases, and the blood vessel region may be masked. In other words, the detecting unit 142 corresponds to an example of a mask processing unit configured to mask a predetermined region of an eye fundus image.

There are various known methods for extraction of a blood vessel region. One method using an AO-SLO image may include dividing brightness before and after a frame for each corresponding pixel and acquiring a region having a large dispersion as a result as a blood vessel region. Alternatively, a blood vessel region may be detected from an image with a larger field angle than that of the WF-SLO image, and the result of the positioning performed in step S230 may be reflected thereon. Then, the blood vessel region on the AO-SLO image may be acquired.

When the identification of a blood vessel or other effects such as a disease is not necessary, a region having a low brightness on a subject AL-SLO image or a region having a low signal indicative of a periodicity inherent to photoreceptor cells acquired by performing frequency conversion on the AO-SLO image may be detected for masking.

The detecting unit 142 stores information on the thus acquired mask region in which photoreceptor cell detection is not performed in the storage unit 130 through the control unit 120. Subsequently, the mask region may be acquired simultaneously with the acquisition of the AO-SLO image, and processing may be performed on an unmasked region only as a subject. More specifically, in step S240, the detecting unit 142 acquires candidate points for a plurality of photoreceptor cells from a region other than a region masked by a mask processing unit from an eye fundus image.

Fifth Exemplary Embodiment

According to the first to fourth exemplary embodiments, the processing is performed on a subject AO-SLO image entirely. However, defining an entire image as a subject may result in low accuracy in a case where the field angle of the image is wide or case where a region having a large change in density of photoreceptor cells near the fovea is defined as a subject of the analysis. In step S720, the MFNND is acquired from an NND distribution, for example. However, the value may be significant different between a region having a significantly high density near the fovea and a region far away from the fovea.

In such a case, the image may be divided into sub-regions for the analysis in accordance with the state (such as a distance from the fovea) of the region to be analyzed or the field angle of imaging. The size of the region in this case preferably is preferably allowing the region to contain appropriately 200 photoreceptor cells but may be changed in accordance with the intended accuracy.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that these exemplary embodiments are not seen to be limiting. The scope of the following claims is to be accorded the broadest interpretation so as to encompass all such modifications and equivalent structures and functions.

This application claims the benefit of Japanese Patent Application No. 2014-254601, filed Dec. 16, 2014, which is hereby incorporated by reference herein in its entirety.

What is claimed is:

1. An ophthalmic apparatus comprising:
    an image acquiring unit configured to acquire an eye fundus image of an eye to be examined;
    a candidate acquiring unit configured to acquire a plurality of candidate points for a photoreceptor cell in the eye fundus image based on brightness values of the eye fundus image;
    a first acquiring unit configured to acquire a first feature value of a first candidate point included in the plurality of candidate points based on a distance between the first candidate point and a second candidate point included in the plurality of candidate points; and
    a determining unit configured to determine whether the first candidate point is a point representing the photoreceptor cell or not based on the first feature value.

2. The ophthalmic apparatus according to claim 1, wherein the first acquiring unit acquires the first feature value based on a distance between a position of the first candidate point and the fovea in the eye fundus of the eye to be examined and a distance between the first candidate point and the second candidate point.

3. The ophthalmic apparatus according to claim 2, wherein the first acquiring unit acquire the first feature value based on a reference distance between photoreceptor cells, which is acquired based on distances between the positions of the candidate points and the fovea in the eye fundus of the eye to be examined and the distance between the first candidate point and the second candidate point.

4. The ophthalmic apparatus according to claim 3, wherein the first acquiring unit acquires the first feature value based on a difference between the distance between the first candidate point and the second candidate point and the reference distance.

5. The ophthalmic apparatus according to claim 4, wherein, as the difference decreases, the first feature value changes to a value representing the probability that the first candidate point is a photoreceptor cell.

6. The ophthalmic apparatus according to claim 1, wherein the first acquiring unit acquires the first feature value based on an average value of distances between the first candidate point and at least two candidate points including the second candidate point among the plurality of candidate points.

7. The ophthalmic apparatus according to claim 1, further comprising a second acquiring unit configured to acquire a second feature value different from the first feature value based on the brightness of the first candidate point,
wherein the determining unit determines whether the first candidate point is a point representing the photoreceptor cell or not based on the first feature value and the second feature value.

8. The ophthalmic apparatus according to claim 1, further comprising a second acquiring unit configured to acquire a second feature value different from the first feature value based on the first candidate point and the second candidate point,
wherein if the determining unit determines, based on the second feature value, that the first candidate point is not a point representing the photoreceptor cell and the second candidate point is a point representing the photoreceptor cell, the determining unit determines, based on the first feature value, whether the first candidate point is a point representing the photoreceptor cell or not.

9. The ophthalmic apparatus according to claim 1, further comprising an adding unit configured to add a candidate point based on the distance between the first candidate point and the second candidate point.

10. The ophthalmic apparatus according to claim 1, further comprising a mask processing unit configured to mask a predetermined region of the eye fundus image,
wherein the candidate acquiring unit acquires the plurality of candidate points for a photoreceptor cell in a region other than the region masked by the mask processing unit in the eye fundus image.

11. The ophthalmic apparatus according to claim 1, further comprising a display control unit configured to cause a display unit to display the eye fundus image and a candidate point that is determined by the determining unit to be a point representing the photoreceptor cell.

12. The ophthalmic apparatus according to claim 8, further comprising a display control unit configured to cause a display unit to display the first candidate point and the second candidate point in different display forms if the determining unit determines, based on the first feature value, that the first candidate point is a point representing the photoreceptor cell.

13. The ophthalmic apparatus according to claim 1, wherein the second candidate point is a point neighboring to the first candidate point.

14. A photoreceptor cell detection method comprising:
acquiring an eye fundus image of an eye to be examined;
acquiring a plurality of candidate points for a photoreceptor cell in the eye fundus image based on brightness values of the eye fundus image;
acquiring a first feature value of a first candidate point included in the plurality of candidate points based on a distance between the first candidate point and a second candidate point included in the plurality of candidate points; and
determining whether the first candidate point is a point representing the photoreceptor cell or not based on the first feature value.

15. A non-transitory computer-readable storage medium storing computer-executable instructions for causing a computer to execute a photoreceptor cell detection method comprising:
acquiring an eye fundus image of an eye to be examined;
acquiring a plurality of candidate points for a photoreceptor cell in the eye fundus image based on brightness values of the eye fundus image;
acquiring a first feature value of a first candidate point included in the plurality of candidate points based on a distance between the first candidate point and a second candidate point included in the plurality of candidate points; and
determining whether the first candidate point is a point representing the photoreceptor cell or not based on the first feature value.

* * * * *